US005882689A

United States Patent [19]
Lajoie et al.

[11] Patent Number: 5,882,689
[45] Date of Patent: Mar. 16, 1999

[54] CONTROL OF SOILBORNE FUNGI IN CULTIVATED CROPS

[75] Inventors: M. Steven Lajoie, Basking Ridge, N.J.; Carl E. Henry, Yardley, Pa.

[73] Assignee: Church & Dwight Co., Inc., Princeton, N.J.

[21] Appl. No.: 997,352

[22] Filed: Dec. 23, 1997

[51] Int. Cl.$^6$ .......................... A01N 59/00; A01N 59/06; A01N 25/12; A01N 25/14

[52] U.S. Cl. .......................... 424/717; 424/405; 424/407; 424/409; 424/417; 424/421; 424/489; 424/683; 424/686; 424/687; 424/715; 424/716; 514/517; 514/547; 514/709; 514/710; 514/711; 514/769; 514/770; 514/772; 514/772.3; 514/777; 514/778; 514/780; 514/781; 514/782; 514/951; 514/952

[58] Field of Search ..................................... 424/717, 683, 424/686, 687, 715, 716, 405, 409, 407, 417, 421, 489; 514/517, 547, 709–711, 769, 770, 772, 772.3, 777, 780, 778, 781, 782; 504/101

[56] References Cited

U.S. PATENT DOCUMENTS

| | | | |
|---|---|---|---|
| 1,560,558 | 11/1925 | Fulton et al. | 424/715 |
| 4,599,233 | 7/1986 | Misato et al. | 424/127 |
| 5,415,877 | 5/1995 | Winston | 424/717 |
| 5,425,952 | 6/1995 | Winston | 424/717 |
| 5,432,146 | 7/1995 | Winston | 504/101 |
| 5,432,148 | 7/1995 | Winston | 504/101 |
| 5,468,715 | 11/1995 | Joseph et al. | 504/101 |
| 5,468,716 | 11/1995 | Winston | 504/101 |

OTHER PUBLICATIONS

Peanut Science, 17, 28–31, (1990).

The American Phytopathological Soc., 72, 635–639 (1982).

Oklahoma Peanut, p. 5 (1992).

*Primary Examiner*—John Pak
*Attorney, Agent, or Firm*—Irving Fishman

[57] ABSTRACT

This invention provides a method for controlling soilborne fungal disease in cultivated field plants such as a peanut crop. Field crop soil is treated with a free-flowing granular fungicide composition which can be applied by aerial means with minimal settling on plant foliage. The granular fungicide composition comprises ammonium bicarbonate and a solid surfactant ingredient, and is effective against soilborne fungi such as a Sclerotinia, Rhizoctonia, Pythium, Fusarium, Phytophthora or Verticillium species.

22 Claims, No Drawings

CONTROL OF SOILBORNE FUNGI IN CULTIVATED CROPS

BACKGROUND OF THE INVENTION

The control of phytopathogenic fungi is of great economic importance since fungal growth on plants or on parts of plants inhibits production of root, stem, foliage, fruit or seed, and the overall quality of a cultivated crop. About 25 percent of all fungal diseases in agriculture and horticulture are caused by powdery mildew phytopathogens.

Because of the vast economic ramifications of fungal propagation in agricultural and horticultural cultivations, a broad spectrum of fungicidal and fungistatic products have been developed for general and specific applications.

Of background interest with respect to the present invention embodiments are fungicide compositions which contain an inorganic bicarbonate and an optional carbonate compound. It is known that bicarbonate and carbonate compounds exhibit fungicidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillium italicum* and *Penicillium digitatum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

U.S. Pat. No. 4,599,233 describes a fungicide composition which consists of sodium bicarbonate in combination with a surface active food emulsifier such as sorbitan monostearate.

Japanese patent 53118523 describes the combination of sodium bicarbonate and lecithin as an active agent for the control of agricultural and fruit storage fungus diseases.

Japanese patent 56043207 describes a biocidal composition containing sodium bicarbonate and a polyglycerol fatty acid ester. The biocide controls *Penicillium digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

German patent DE 2927994 describes a fungicide which consists of sodium bicarbonate incorporated into a food-compatible surfactant such as saccharose laurate.

Japanese patent 57062208 describes horticultural fungicides in which the addition of sodium bicarbonate to polyoxin or thiophanatemethyl increases the fungicidal activity of the organic biocide against *Botrytis cinerea* on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wilt, rice sheath blight, rice blast and citrus canker.

Of particular interest with respect to the present invention is the control of soilborne phytopathogenic fungi. Soilborne diseases are of significant economic importance to peanut industries in Oklahoma and other areas of the United States. These diseases include Sclerotinia blight (*Sclerotinia minor* Jagger), southern blight (*Schlerotium rolfsii* sacc.) and pod rot (*Pythium myriotylum* and *Rhizoctonia solani* Kuehn).

Fungicides are the common means of soilborne disease management in peanut crops. Because of increasing environmental and health related concerns, the use of organic pesticides is becoming increasingly tenuous, and there is substantial incentive to investigate the development of new fungicide products.

Ammonium bicarbonate has been applied by chemical spray application equipment to peanut field crops for control of Sclerotinia blight. Under the application conditions, the ammonium bicarbonate was phytotoxic, as evidenced by a reduction in peanut yield [Peanut Science, 17, 28 (1990)].

There is a continuing need for improved methods for providing preventive and curative fungicidal activity for the protection of cultivated plants with a minimum of phytotoxic side effects.

Accordingly, it is an object of this invention to provide a fungicide composition which can be applied effectively to cultivated plants, and which is within acceptable limits with respect to environmental and health concerns.

It is another object of this invention to provide a method of controlling fungi in cultivated field crops with a minimum of phytotoxic side effects.

It is a further object of this invention to provide a method for controlling soilborne Sclerotinia blight and other diseases in peanut crops by means of an ecologically safe inorganic fungicide with an acceptable degree of phytotoxic side effects.

Other objects and advantages of the present invention shall become apparent from the accompanying description and examples.

DESCRIPTION OF THE INVENTION

One or more objects of the present invention are accomplished by the provision of a method for controlling soilborne fungal disease in cultivated field crops which comprises contacting the crop soil with a fungicidally effective application of a free-flowing granular composition comprising between about 75–99.6 weight percent of ammonium bicarbonate, and between about 0.4–25 weight percent of a solid surfactant ingredient selected from the group consisting of alkali metal and ammonium $C_{10}$–$C_{30}$ aliphatic-containing carboxylate, sulfonate, sulfate and phosphate salts; wherein the granular composition has a bulk density between about 55–65 pounds per cubic foot, and the granules have a particle size distribution substantially in the range between about 900–3000. In a preferred embodiment the ammonioum bicarbonate comprises at least about 98 weight % and the solid surfactant is no greater than about 2 weight %

In another embodiment this invention provides a free-flowing granular fungicide composition comprising between about 98–99.6 weight percent of ammonium bicarbonate, and between about 0.4–2 weight percent of a solid surfactant ingredient selected from the group consisting of alkali metal and ammonium $C_{10}$–$C_{30}$ aliphatic-containing carboxylate, sulfonate, sulfate and phosphate salts; wherein the granular composition has a bulk density between about 55–65 pounds per cubic foot, and the granules have a particle size distribution substantially in the range between about 900–3000 microns.

Besides the advantage of surface activity when an invention fungicide composition is applied to a field crop, the surfactant ingredient functions as an anti-caking agent in the fungicide product, and it limits the hygroscopic absorption of atmospheric moisture by the ammonium bicarbonate ingredient prior to application. A present invention granular fungicide composition is free-flowing under ambient atmospheric conditions of humidity and temperature.

An invention granular fungicide composition can be applied to a standing field crop by aerial means with an aircraft. Because of the relatively large size and high density of the granule particles, the fungicide composition can be applied to a target crop area with little or no drifting loss of fungicide composition. Alternatively, the product according to the invention can be applied by broadcasting or chemigation methods, but generally aerial methods are preferred.

As another significant advantage, the applied granule particles do not adhere or settle on the plant foliage. This serves to prevent phytotoxic damage to the plant foliage.

After a present invention fungicide composition is applied to the soil of a field crop, it can be followed by the application of irrigation water to diffuse the composition into the root-bound soil.

The applied fungicide composition also can be slow-released into the root-bound substrate by the action of atmospheric humidity, or by rainfall.

Optionally, the fungicide composition on the soil surface can be incorporated into the root-bound substrate by a tilling operation. Similarly, the fungicide composition can be used as a soil fumigant, especially when utilized prior to or during the planting operation.

A present invention granular fungicide composition is particularly effective for controlling soilborne fungi which are associated with peanut crops. An invention fungicide composition inhibits the destructive effect on peanut crops of soilborne fungi which include Sclerotinia, Rhizoctonia, Pythium, Fusium, *S. rolfsii*, Phytophthora and Verticillium species. Increased peanut yields are obtained from the treated peanut crops.

A surfactant is an essential ingredient in a present invention granular fungicide composition. It functions as an anti-caking agent in the ammonium bicarbonate granules, and it contributes to the dispersion of the ammonium bicarbonate in the soil in the presence of moisture.

The surfactant ingredient of an invention fungicide formulation is an anionic surface active derivative selected from alkali metal and ammonium $C_{10}$–$C_{30}$ aliphatic-containing carboxylate, sulfonate, sulfate and phosphate salts. These anionic surfactants provide superior dispersant activity when an invention fungicide composition interacts with moisture in the soil.

Surfactants which provide suitable dispersant properties are anionic compounds such as alkyl sulfates and alkyl ether sulfates having 10–20 carbon atoms in the alkyl group. The ether sulfates can contain about 1–10 oxyethylene groups in the molecule. The sulfate surfactants can be in the form of sodium, potassium, ammonium, lower alkylamine or lower alkanolamine salts. Amine compounds are illustrated by dimethylamine, trimethylamine, diethanolamine, triethanolamine, and the like.

Other suitable anionic surfactants include sodium, potassium and ammonium alkylbenzenesulfonates, in which the alkyl group contains about 9–15 carbon atoms; sodium alkyl glycerol ether sulfonates; sodium coconut oil fatty acid monoglyceride sulfates and sulfonates; sodium salts of sulfuric acid esters of oxyethylated fatty alcohols; sodium sulfosuccinate esters; condensation products of fatty acids with sarcosine; monoester or diester phosphates of $C_{12}$–$C_{18}$ fatty alcohols in the form of sodium, potassium or ammonium salts (e.g., Gafac PE-510, GAF Corporation); and the like. Anionic surfactants are described in references such as U.S. Pat. No. 4,528,039 and U.S. Pat. No. 5,037,818; incorporated herein by reference.

Other suitable anionic surfactants are $C_{12}$–$C_{22}$ fatty acid salts selected from alkali metal and ammonium salts of natural straight chain and synthetic branched chain fatty acids, which have a saturated or unsaturated structure. Illustrative of natural fatty acids are myristic acid, palmitic acid, stearic acid, oleic acid, linoleic acid, arachidic acid, bohenic acid, cetoleic acid, and the like.

A $C_{12}$–$C_{22}$ fatty acid salt ingredient can consist of two or more saturated or unsaturated carboxylic acids such as those derived from beef and mutton tallow, lard, cottonseed oil, palm oil, and the like.

Preferred anionic surfactants are selected from the group consisting of sodium, potassium and ammonium $C_8$–$C_{14}$ dialkyl sulfosuccinate and $C_{10}$–$C_{20}$ alkyl sulfate salts, singly or in any combination. Illustrative of a particularly preferred surfactant ingredient is an admixture of sodium, potassium or ammonium dioctyl sulfosuccinate and sodium, potassium or ammonium lauryl sulfate salts.

A present invention granular fungicide composition can be produced utilizing conventional equipment and procedures. Ammonium bicarbonate and surfactant powders can be blended, compacted and granulated to produce an invention fungicide product.

Typically, a blend of ammonium bicarbonate powder and surfactant powder is compacted by mechanical densification equipment into a thin sheet having a thickness of about one-sixteenth to three-eights inch. A convenient method of compacting is to pass the powder blend between two cylindrical rolls which exert a pressure between about 1000–4000 psi.

The continuous thin sheet from the compactor is fed to a flaking unit to form flake-like particles, which in turn are passed through a crusher to provide granule particles that are screened to meet particle size specifications.

A preferred granular fungicide composition of the present invention has a bulk density between about 55–65 pounds per cubic foot, and the granules have a specific density between about 1.5–2.5 grams per cubic centimeter, and a particle size distribution between about 900–3000 microns.

A present invention free-flowing granular fungicide product is adapted for application by aerial or ground spreading means to field crops to prevent or eradicate soilborne fungal disease, or to inhibit re-infection by phytopathogenic fungi or reduce the viability of the fungi in the soil so the intensity of the disease will be reduced during the next growing season, even without retreatment. Typically, the fungicide product is applied to a standing field crop at least twice during the growth cycle, with a time interval between about 5–20 days.

The following examples are further illustrative of the present invention. The components and specific ingredients are presented as being typical, and various modifications can be derived in view of the foregoing disclosure within the scope of the invention.

EXAMPLE I

This Example illustrates the preparation of a free-flowing granular fungicide composition in accordance with the present invention.

A full-scale manufacturing facility is employed for production of free-flowing granular ammonium bicarbonate product.

An ammonium bicarbonate powder (average particle size: 200 microns; Norsk) is blended with 1.0 weight percent of sodium dioctyl sulfosuccinate (Geropon SDS; Rhone Poulenc).

The blended starting material enters the processing system via a bag-dump station and a one-story bucket elevator. Horizontal and vertical screws convey the material to a 7×10 Fitzpatrick compactor.

The output from the compactor is fed into a Fitzmill equipped with a 0312 screen. The product from the mill is passed into a Sweco screener outfitted with Market Grade screens of 6 and 18 mesh. The −6/+20 mesh fraction is packaged, and all fine and coarse material is recycled to the compactor.

The particle size distribution of the product is as follows:

| Mesh Size | Cum. Wt. % |
|---|---|
| 6 | 0.0 |
| 16 | 82.4 |
| 20 | 95.6 |
| PAN | 100.0 |

The granular ammonium bicarbonate product has a bulk density of 63.8 pounds per cubic foot, and a specific density of 1.6 grams per cubic centimeters. The product is composed of non-tacky hard granules which are free-flowing.

EXAMPLE II

This Example illustrates the application of a present invention free-flowing granular ammonium bicarbonate fungicide composition to a peanut field crop for effective control of soilborne fungi.

As summarized in Tables I–III, treatments and application methods include an untreated control (UTC), chemigation with a slow-release wettable powder-type ammonium bicarbonate formulation, and ground and aerial applications with a compacted, granular ammonium bicarbonate formulation.

The comparative data demonstrate the feasibility and efficacy of both ground aerial applications of a present invention granular ammonium bicarbonate composition.

TABLE I

COMPARISON OF AMMONIUM BICARBONATE FORMULATIONS AND APPLICATION METHODS FOR CONTROL OF SCLEROTINIA BLIGHT, PEANUT cv. FLORUNNER

| APPLICATION METHOD[a] | ABC RATE/ ACRE[f] | DISEASE INCIDENCE[g,h,i] | YIELD/ ACRE[f,k,j] | VALUE/ ACRE[h,k] |
|---|---|---|---|---|
| UTC[b] | 0 | 39% | 842 | $497 |
| CHEMIGATION[c] | 100 | 11% | 3033 | 1789 |
| GROUND[d] | 100 | 14% | 3050 | 1800 |
| AIR[e] | 100 | 13% | 3008 | 1775 |

[a]Treatment plots consisted of 20 planting rows (60-ft.) × 425-ft. (25,500-ft.$^2$), and were replicated three times in a completely random design.
[b]UTC-untreated control; received about 1.5-in. overhead irrigation.
[c]A non-compacted, wettable powder-type ammonium bicarbonate (ABC) formulation was dissolved and applied by chemigation in about 1.5-in. overhead irrigation.
[d]A compacted, granular-type ABC formulation was applied as a broadcast treatment with a ground-driven fertilizer applicator. Treatments were soil incorporated within 24-hrs. following application with about 1.5-in. overhead irrigation.
[e]A compacted, granular-type ABC formulation was applied as a broadcast treatment dropped from an altitude of about 20-ft. by an airplane implemented with fertilizer spreader equipment. Treatments were soil incorporated within 24-hrs. following application with about 1.5-in. overhead irrigation.
[f]Numbers within the column represent pounds/acre.
[g]Disease incidence (% Sclerotinia blight) = observed number of infection sites/100-ft. windrow + 200 potential infection sites/100-ft. windrow × 100%.
[h]Numbers within the column are mean values of three replications and rounded to the nearest whole number. Deviation in treatments was determined by analysis of variance. Significant differences in treatments were identified by Schoffe's method of multiple comparison and corresponding $Ss_q$ values at the 95% confidence level (P = 0.05).
[i]$Ss_q$ (0.05) = 22.79 (means within the column differing by more than 22.79 units are significantly different at the 95% confidence level.
[j]$Ss_q$ (0.05) = 1901 (means within the column differing by more than 1901 units are significantly different at the 95% confidence level).
[k]Value/acre was determined by USDA and state grading standards, and based on a unit price of $0.59/lb. $SS_q$ (0.05) = 1108 (means within the column differing by more than 1108 units are significantly different at the 95% confidence level).

TABLE II

COMPARISON OF AMMONIUM BICARBONATE FORMULATIONS AND APPLICATION METHODS FOR CONTROL OF SCLEROTINIA BLIGHT AND SOUTHERN BLIGHT, PEANUT cv. FLORUNNER

| APPLICATION METHOD[a] | ABC RATE/ ACRE[f] | DISEASE INCIDENCE[g,h] | | YIELD/ ACRE[f,h,k] | VALUE/ ACRE[h,l] |
|---|---|---|---|---|---|
| | | SCB[i] | SOB[j] | | |
| UTC[b] | 0 | 28% | 23% | 958 | $594 |
| CHEMIGATION[c] | 100 | 10% | 6% | 2825 | 1752 |
| GROUND[d] | 100 | 9% | 4% | 2933 | 1818 |
| AERIAL[e] | 100 | 7% | 8% | 2867 | 1778 |

[a]Treatment plots consisted of 20 planting rows (60-ft.) × 500-ft. (= 30,000-ft.$^2$), and were replicated three times in a completely random design.
[b]UTC-untreated control; received about 1.5-in. overhead irrigation.
[c]A non-compacted, wettable powder-type ammonium bicarbonate (ABC) formulation was dissolved and applied by chemigation in about 1.5-in. overhead irrigation.
[d]A compacted, granular-type ABC formulation was applied as a broadcast treatment with a ground-driven fertilizer applicator. Treatments were soil incorporated within 24-hrs. following application with about 1.5-in. overhead irrigation.
[e]A compacted, granular-type ABC formulation was applied as a broadcast treatment dropped from an altitude of approximately 20-ft. by an airplane implemented with fertilizer spreader equipment. Treatments were soil incorporated within 24-hrs. following application with about 1.5-in. overhead irrigation.
[f]Numbers within the column represent pounds/acre.
[g]Disease incidence (% Sclerotinia blight, % southern blight) = observed number of infection sites/100-ft. windrow + 200 potential infection sites/100-ft. windrow × 100%.
[h]Numbers within the column are mean values of three replications and rounded to the nearest whole number. Deviation in treatments was determined by analysis of variance. Significant differences in treatments were identified by Schoffe's method of multiple comparison and corresponding $Ss_q$ (0.05) = 16.43 (means within the column differing by more than 16.43 units are significantly different at the 95% confidence level).
[i]SCB = Sclerotinia blight. $Ss_q$ (0.05) = 16.43 (means within the column differing by more than 16.43 units are significantly different at the 95% confidence level).
[j]SOB = Sclerotinia blight. $Ss_q$ (0.05) = 14.09 (means within the column different by more than 14.07 units are significantly different at the 95% confidence level).
[k]$Ss_q$ (0.05) = 1849 (means within the column differing by more than 1819 units are significantly different at the 95% confidence level.
[l]Value/acre was determined by USDA and state grading standards and based on a unit price of $0.62/lb. $Ss_q$ (0.05) = 1025 (means within the column differing by more than 1025 units are significantly different at the 95% confidence level).

TABLE III

COMPARISON OF AMMONIUM BICARBONATE FORMULATIONS AND APPLICATION METHODS FOR CONTROL OF SCLEROTINIA BLIGHT AND SOUTHERN BLIGHT, PEANUT cv. FLORUNNER

| APPLICATION METHOD[a] | ABC RATE/ ACRE[f] | DISEASE INCIDENCE[g,h] | | YIELD/ ACRE[f,h,k] | VALUE/ ACRE[h,l] |
|---|---|---|---|---|---|
| | | SCB[i] | SOB[j] | | |
| UTC[b] | 0 | 21% | 17% | 1133 | $680 |
| CHEMIGATION[c] | 100 | 6% | 8% | 2450 | 1470 |
| GROUND[d] | 100 | 5% | 5% | 2417 | 1450 |
| AERIAL[e] | 100 | 6% | 4% | 2458 | 1475 |

[a]Treatment plots consisted of 20 planting rows (60-ft.) × 500-ft. (= 30,000 ft.$^2$), and were replicated three times in a completely random design.
[b]UTC-untreated control; received about 1.5-in. overhead irrigation.
[c]A non-compacted, wettable powder-type ammonium bicarbonate (ABC) formulation was dissolved and applied by chemigation in about 1.5-in. overhead irrigation.
[d]A compacted, granular-type ABC formulation was applied as a broadcast treatment with a ground-driven fertilizer applicator. Treatments were soil incorporated within 24-hrs. following application with about 1.5-in. overhead irrigation.

TABLE III-continued

COMPARISON OF AMMONIUM BICARBONATE FORMULATIONS AND APPLICATION METHODS FOR CONTROL OF SCLEROTINIA BLIGHT AND SOUTHERN BLIGHT, PEANUT cv. FLORUNNER

| APPLICATION METHOD[a] | ABC RATE/ ACRE[f] | DISEASE INCIDENCE[g,h] | | YIELD/ ACRE[f,h,k] | VALUE/ ACRE[h,l] |
|---|---|---|---|---|---|
| | | SCB[i] | SOB[j] | | |

[e]A compacted, granular-type ABC formulation was applied as a broadcast treatment dropped from an altitude of approximately 20-ft. by an airplane implemented with fertilizer spreader equipment. Treatments were soil incorporated within 24-hrs. following application with about 1.5-in. overhead irrigation.
[f]Numbers within the column represent pounds/acre.
[g]Disease incidence (% Sclerotinia blight, % southern blight) = observed number of infection sites/100-ft. windrow ÷ 200 potential infection sites/100-ft. windrow × 100%.
[h]Numbers within the column are mean values of three replications and rounded to the nearest whole number. Deviation in treatments was determined by analysis of variance. Significant differences in treatments were identified by Schoffe's method of multiple comparison and corresponding $Ss_q$ values at the 95% confidence level (P = 0.05).
[i]SCB = Sclerotinia blight. $Ss_q$ (0.05) = 13.31 (means within the column differing by more than 13.31 units are significantly different at the 95% confidence level).
[j]SOB = Sclerotinia blight. $Ss_q$ (0.05) = 7.59 (means within the column different by more than 7.59 units are significantly different at the 95% confidence level).
[k]$Ss_q$ (0.05) = 1218 (means within the column differing by more than 1218 units are significantly different at the 95% confidence level).
[l]Value/acre was determined by USDA and state grading standards and based on a unit price of $0.62/lb. $Ss_q$ (0.05) = 721 (means within the column differing by more than 721 units are significantly different at the 95% confidence level).

What is claimed is:

1. A method for controlling soilborne fungal disease in cultivated field crops which comprises contacting the crop soil with a fungicidally effective application of a free-flowing granular composition comprising between about 75–99.6 weight percent of ammonium bicarbonate, and between about 0.4–25 weight percent of a solid surfactant ingredient selected from the group consisting of alkali metal and ammonium $C_{10}$–$C_{30}$ aliphatic-containing carboxylate, sulfonate, sulfate and phosphate salts; wherein the granular composition has a bulk density between about 55–65 pounds per cubic foot, and the granules have a particle size distribution substantially in the range between about 900–3000 microns.

2. The method of claim 1 wherein the granular composition is applied by means of a ground or aerial means.

3. The method of claim 2 wherein said granular composition is applied by at least one means selected from broadcasting, chemigation, and aerial application means.

4. The method of claim 1 wherein the application of granular composition to the soil is followed by a tiller operation.

5. The method of claim 1 wherein the application of granular composition to the soil is followed by the application of irrigation water.

6. The method of accordance with claim 1 wherein the granular composition applied to the soil is slow-released and diffused into the root-bound substrate under ambient moisture conditions.

7. The method of claim 1 wherein the soilborne fungal disease is a Sclerotinia, Rhizoctonia, Pythium, Fusarium, Phytophthora or Verticillium species.

8. The method of claim 1 wherein the application of granular composition is to the root-bound soil of a peanut field crop.

9. The method of claim 1 wherein the surfactant ingredient comprises alkali metal or ammonium $C_8$–$C_{14}$ dialkyl sulfosuccinate salt.

10. The method of claim 1 wherein the surfactant ingredient comprises alkali metal or ammonium $C_{10}$–$C_{20}$ alkyl sulfate salt.

11. The method of claim 1 wherein the surfactant ingredient comprises a mixture of alkali metal or ammonium $C_8$–$C_{14}$ dialkyl sulfosuccinate and $C_{10}$–$C_{20}$ alkyl sulfate salts.

12. The method of claim 1 wherein said granular composition is applied to said soil pre-crop planting.

13. The method of claim 1 wherein said granular composition is applied to said soil during a planting operation.

14. The method of claim 1 wherein said granular composition is applied to said soil post-planting, but pre-emergence of said crop.

15. The method of claim 1 wherein said granular composition is applied to said soil post crop emergence.

16. A free-flowing granular fungicide composition comprising between about 75–99.6 weight percent of ammonium bicarbonate, and between about 0.4–25 weight percent of a solid surfactant ingredient selected from the group consisting of alkali metal and ammonium $C_{10}$–$C_{30}$ aliphatic-containing carboxylate, sulfonate, sulfate and phosphate salts; wherein the granular composition has a bulk density between about 55–65 pounds per cubic foot, and the granules have a particle size distribution substantially in the range between about 900–3000 microns.

17. The fungicide composition of claim 16 wherein the surfactant ingredient comprises alkali metal or ammonium $C_8$–$C_{14}$ dialkyl sulfosuccinate.

18. The fungicide composition of claim 16 wherein the surfactant ingredient comprises alkali metal or ammonium $C_{10}$–$C_{20}$ alkyl sulfate salt.

19. The fungicide composition of claim 16 wherein the surfactant ingredient comprises a mixture of alkali metal or ammonium $C_8$–$C_{14}$ dialkyl sulfosuccinate and $C_{10}$–$C_{20}$ alkyl sulfate salts.

20. The fungicide composition of claim 16 wherein the surfactant ingredient comprises sodium, potassium or ammonium dioctyl sulfosuccinate salt.

21. The fungicide composition of claim 16 wherein the surfactant ingredient comprises sodium, potassium or ammonium lauryl sulfate salt.

22. The fungicide composition of claim 16 wherein the surfactant ingredient comprises a mixture of sodium, potassium or ammonium dioctyl sulfosuccinate and sodium, potassium or ammonium lauryl sulfate salts.

* * * * *